US00PP08608P

United States Patent [19]

Machin

[11] Patent Number: Plant 8,608

[45] Date of Patent: Feb. 22, 1994

[54] CHRYSANTHEMUM PLANT NAMED TEIDE

[75] Inventor: Barrie J. Machin, Lee-on-Solent, England

[73] Assignee: Goldstock Breeding Limited, Hants, England

[21] Appl. No.: 952,976

[22] Filed: Sep. 29, 1992

[51] Int. Cl.[5] ..... A01H 5/00

[52] U.S. Cl. ..... Plt./77

[58] Field of Search ..... Plt. 77

References Cited

U.S. PATENT DOCUMENTS

Plt. 3401 9/1973 Machin .....Plt./77

Plt. 5440 4/1985 Duffett .....Plt./77

*Primary Examiner*—Howard J. Locker

*Attorney, Agent, or Firm*—Foley & Lardner

[57] ABSTRACT

A Chrysanthemum plant named Teide particularly characterized by its classic decorative form, incurving type, pure white ray floret color, diameter across face of capitulum of 69 to 79 mm when fully opened and when grown as a single stem spray cut mum, flowering response under normal temperatures of 63 to 67 days after start of short days, plant height of 91 to 102 cm when grown with 14 long days prior to start of short days, peduncle length of the first lateral at flowering after removing the apical bud and without growth regulator applications, of 8 to 13 cm, peduncle length of the fourth lateral at flowering of 15 to 20 cm, and its terminal spray formation.

3 Drawing Sheets

1

The present invention comprises a new and distinct cultivar of Chrysanthemum, botanically known as *Dendranthema grandiflora*, and referred to by the cultivar name Teide.

Teide was originated from a cross made by the inventor, Barrie J. Machin, in a controlled breeding program in Fareham, England, in 1986.

The female parent of Teide was a seedling referred to as Ballerina, a proprietary line used for breeding purposes. Ballerina can be described as a cut spray mum, decorative type, having a creamy white ray floret color, a diameter of capitulum of 76 to 86 mm when fully open, a flowering response to short days of 61 to 63 days, a plant height of 86 to 96 cm when grown with 14 long days prior to start of short days, a peduncle length of the first lateral of 8 to 15 cm and of the fourth lateral of 15 to 20 cm, and a terminal spray formation. The above characteristics are based on plants grown in Fareham, England.

The male parent of Teide was a seedling identified as Bandolier, which can be described as a cut spray mum, decorative type, having a mauve pink ray floret color, diameter of capitulum of 69 to 79 mm, a flowering response of 59 days, a plant height ranging from 76 to 86 cm when grown with 14 long days prior to start of short days, a peduncle length of the first lateral of 4 to 7 cm, and of the fourth lateral of 7 to 15 cm, and a terminal spray formation. The above characteristics are based on plants grown in Fareham, England.

Teide was discovered and selected as one flowering plant within the progeny of the stated cross by Barrie J. Machin in November 1987, in a controlled environment in Fareham, England.

The first act of asexual reproduction of Ballerina was accomplished when vegetative cuttings were taken from the initial selection in January 1988 in a controlled environment in Fareham, England, by Barrie J. Machin.

Horticultural examination of controlled flowerings of successive plantings has shown that the unique combination of characteristics as herein disclosed for Teide are firmly fixed and are retained through successive generations of asexual reproduction.

Teide has not been observed under all possible environmental conditions. The phenotype may vary somewhat with variations in environment such as temperature, light intensity and daylength, without, however, any variance in the genotype.

2

The following observations, measurements and comparisons describe plants grown in Fareham, England under greenhouse conditions which approximate those generally used in commercial greenhouse practice.

The following traits have been repeatedly observed and are determined to be basic characteristics of Teide, which, in combination, distinguish this Chrysanthemum as a new and distinct cultivar:

1. Incurving form.
2. Decorative type.
3. White ray floret color.
4. Diameter across face of capitulum of 69 to 79 mm when fully opened, when grown as a single stem spray cut mum.
5. Flowering response under normal temperatures is 63 to 67 days after start of short days.
6. Plant height is 91 to 102 cm when grown with 14 long days prior to start of short days.
7. Peduncle length of the first lateral at flowering after removing the apical bud and without growth regulator applications is 8 to 13 cm; peduncle length of the fourth lateral at flowering is 15 to 20 cm.
8. Terminal spray formation.

The accompanying photographic drawings show typical inflorescence and leaf characteristics of Teide, with the colors being as nearly true as possible with illustrations of this type.

Sheet 1 is a color photograph of Teide grown as a single stem spray cut mum.

Sheet 2 is a black and white photograph of three views of the inflorescence of Teide.

Sheet 3 is a black and white photograph showing the upper and under sides of the leaves of Teide at 3 stages of development (mature, intermediate and immature).

Of the commercial cultivars known to the inventory, the most similar in comparison to Teide is the cultivar referred to as Snowdon disclosed in U.S. Plant Pat. No. 3,401. Reference is made to attached Chart A, which compares certain characteristics of Teide to the same characteristics of Snowdon. Similar traits are capitulum form and type, and spray formation. The ray floret color of both cultivars is described as white, but Teide has a brighter white ray floret color than Snowdon. Teide also has a smaller diameter capitulum, slighter later flowering response to short days, and more formal neater flowers.

In the following description color references are made to the Royal Horticultural Society Colour Chart. The color values were determined on plant material grown as a single spray cut mum in Fareham, England on Aug. 11, 1988.

Classification:

*Botanical.*—*Dendranthema grandiflora* cv. Teide.

*Commercial.*—Decorative spray cut mum.

INFLORESCENCE

A. Capitulum:

*Form.*—Incurving.

*Type.*—Decorative.

*Diameter across face.*—69 to 79 mm when fully opened.

B. Corolla of ray florets:

*Color (general tonality from a distance of three meters).*—White.

*Color (upper surface).*—RHS 155A.

*Color (under surface).*—RHS 155D.

*Shape.*—Curving, rounded.

C. Reproductive organs:

*Androecium.*—On disc florets only; very small quantity of pollen.

*Gynoecium.*—Present on disc florets and on all ray florets.

PLANT

A. General appearance:

*Height.*—91 to 102 cm when grown in Fareham, England, with 14 long days, prior to start of short days.

B. Foliage:

*Color (upper surface):*—137B.

*Color (under surface).*—137D.

*Shape.*—See photograph.

CHART A

| CHARACTERISTIC | TEIDE | SNOWDEN |
|---|---|---|
| Ray floret color | Pure white | White |
| Capitulum form and type | Incurving Decorative | Incurving Decorative |
| Diameter across face of capitulum | 76 to 89 mm | 79 to 99 mm |
| Flowering response | 63 to 67 days | 60 to 63 days |
| Plant height (14 long days): | 91 to 102 cm | 111 to 131 cm |
| Peduncle length: | | |
| First lateral | 8 to 13 cm | 10 to 15 cm |
| Fourth lateral | 15 to 20 cm | 15 to 20 cm |
| Spray formation | Terminal | Terminal |

COMPARISONS OF PLANTS GROWN AS SINGLE STEM SPRAY CUT MUMS IN FAREHAM, ENGLAND

I claim:

1. A new and distinct Chrysanthemum plant named Teide, as described and illustrated.

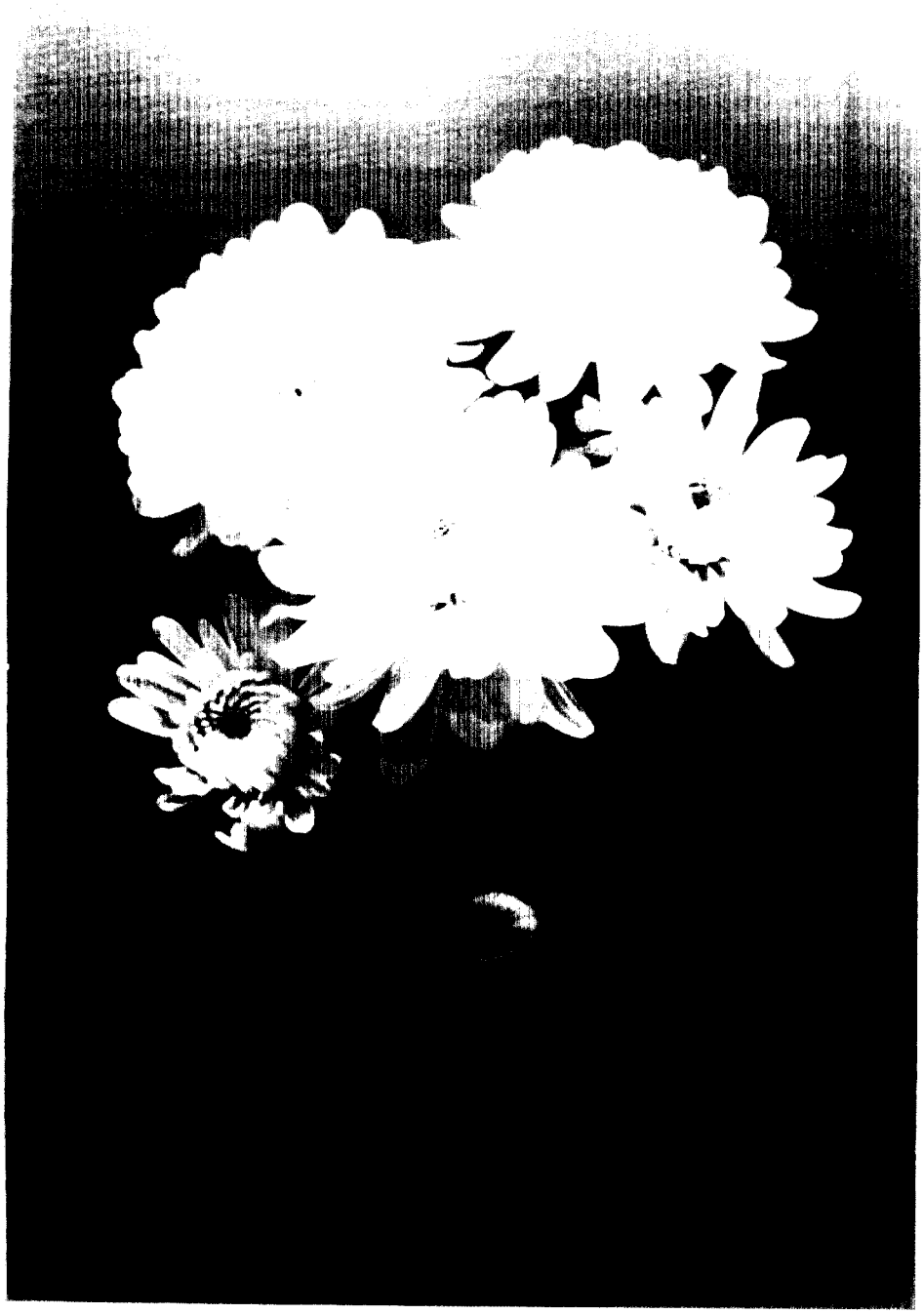

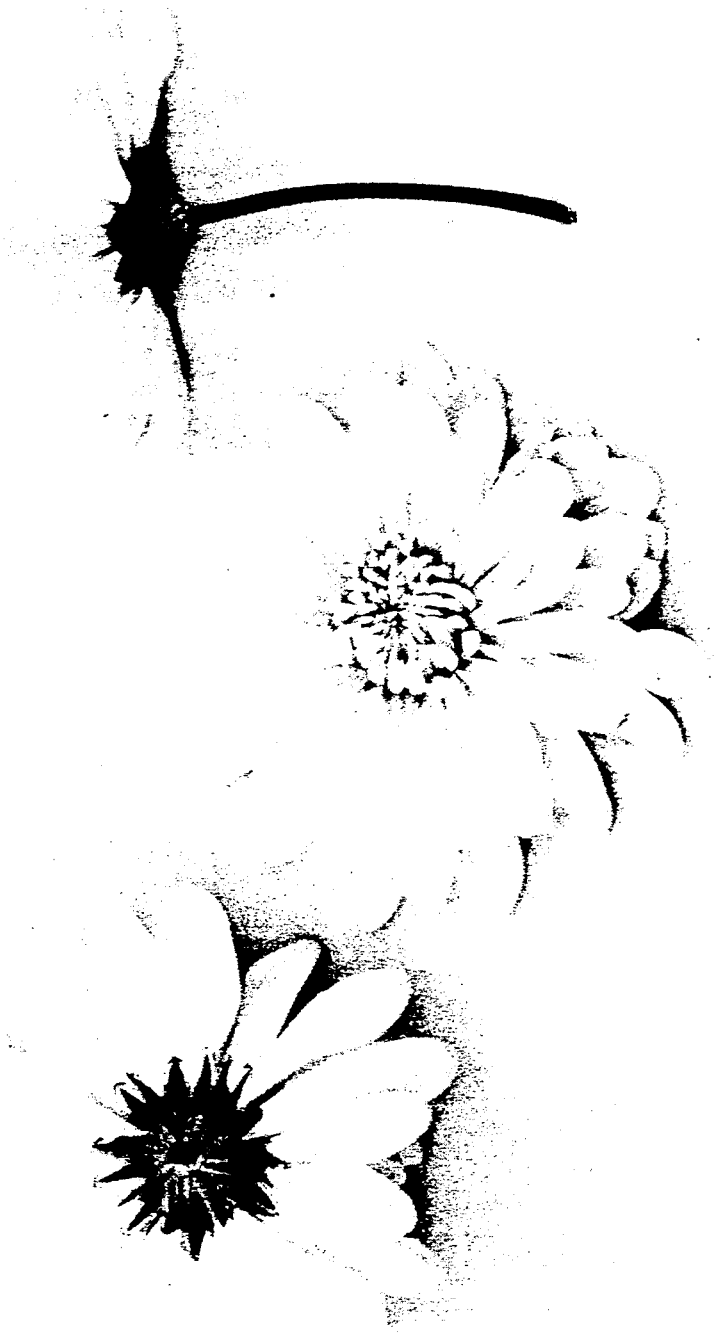

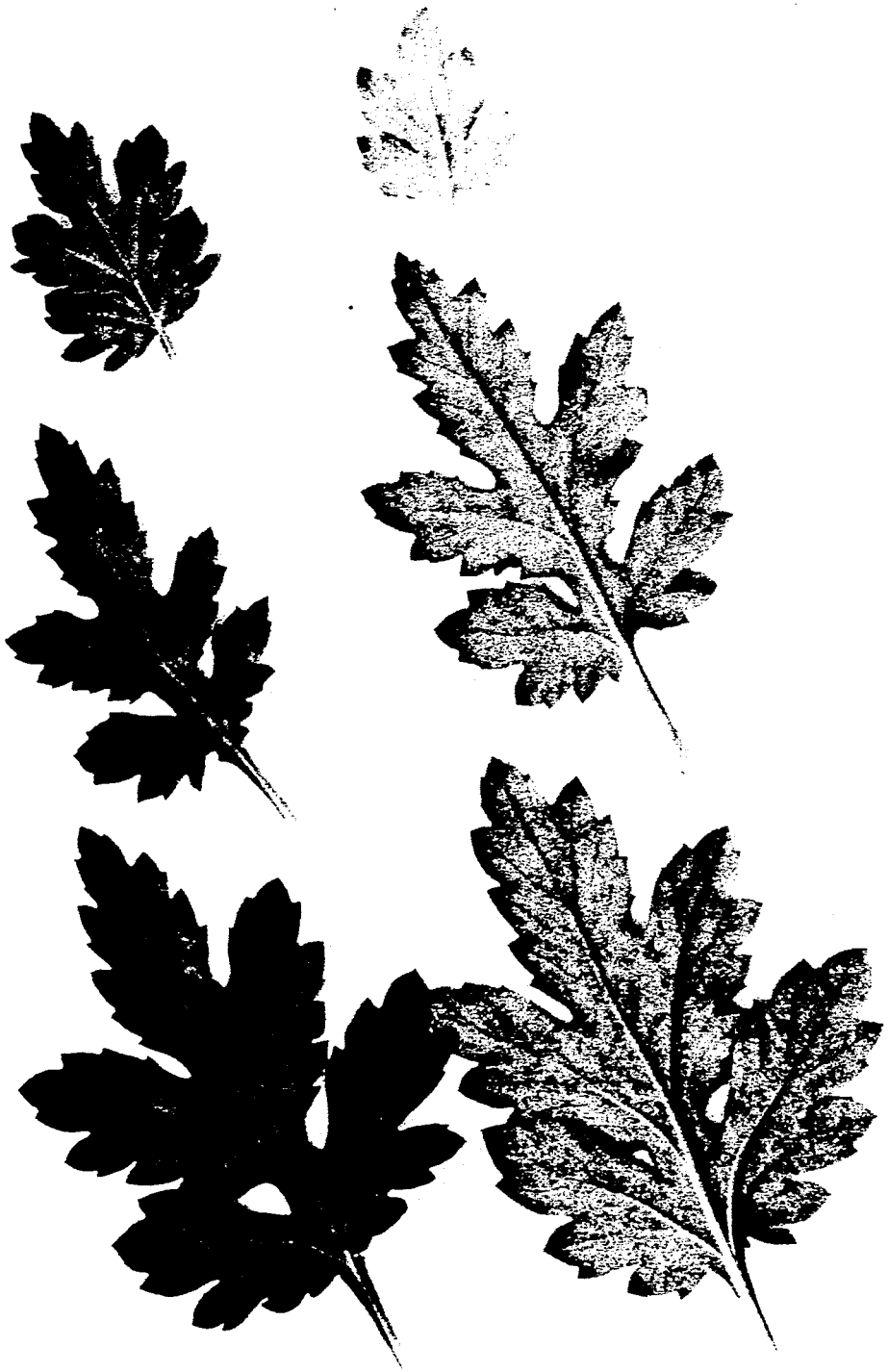

* * * * *